United States Patent
Schraut et al.

(10) Patent No.: US 10,427,150 B2
(45) Date of Patent: Oct. 1, 2019

(54) PIPETTING APPARATUS FOR ASPIRATING AND DISPENSING LIQUIDS

(71) Applicant: BRAND GMBH + CO KG, Wertheim (DE)

(72) Inventors: Jürgen Schraut, Rettersheim (DE); Steffen Gehrig, Walldürn (DE)

(73) Assignee: BRAND GMBH + CO KG, Wertheim (DE)

( * ) Notice: Subject to any disclaimer, the term of this patent is extended or adjusted under 35 U.S.C. 154(b) by 33 days.

(21) Appl. No.: 15/639,034

(22) Filed: Jun. 30, 2017

(65) Prior Publication Data

US 2018/0008975 A1 Jan. 11, 2018

(30) Foreign Application Priority Data

Jul. 5, 2016 (DE) .................... 20 2016 004 140 U (51) Int. Cl.
*B01L 3/02* (2006.01)
*G01N 35/10* (2006.01)
(52) U.S. Cl.
CPC ............. *B01L 3/021* (2013.01); *B01L 3/0237* (2013.01); *G01N 35/1011* (2013.01); *B01L 3/0224* (2013.01)
(58) Field of Classification Search
CPC combination set(s) only.
See application file for complete search history.

(56) References Cited

U.S. PATENT DOCUMENTS 5,947,167 A 9/1999 Bogen et al.
6,180,061 B1 1/2001 Bogen et al.
(Continued)

FOREIGN PATENT DOCUMENTS

DE 43 14 343 A1 11/1994
DE 103 37 484 B4 5/2005
(Continued)

OTHER PUBLICATIONS

Both documents relate to presentations held on an international conference in Jun. 2012 in Bremen, Germany, namely "Actuator 2012, 13th International Conference on New Actuators". The English document "Nanoliter Dispensing on Pipetting Workstations" has almost the same content as the German presentation "Gesundheit".

(Continued)

*Primary Examiner* — Brian R Gordon
(74) *Attorney, Agent, or Firm* — David S. Safran; Roberts Mlotkowski Safran Cole & Calderon, P.C.

(57) ABSTRACT

A pipetting apparatus for aspirating and dispensing liquids having a pipetting unit with an interchangeable vessel that receives a liquid to be transferred, a holder for the pipetting unit, a positioning device for the pipetting unit, a micrometering unit, and an electronic control device. The micrometering unit is embodied separately from the pipetting unit and has a separate electronic control unit. The pipetting unit has a coupling device and the micrometering unit has a counterpart coupling device that matches the coupling device for the purpose of coupling. Coupling device and/or counterpart coupling device is/are switchable. The holder or the micrometering unit has a contact device with at least one electrical contact element and the micrometering unit or the holder has a counterpart contact device, matching the contact device, with at least one counterpart electrical contact element for making electrical contact with the contact element.

13 Claims, 7 Drawing Sheets

(56) References Cited

U.S. PATENT DOCUMENTS

| | | | |
|---|---|---|---|
| 6,232,129 B1 | 5/2001 | Wiktor | |
| 6,599,479 B1* | 7/2003 | Kietzmann | B01L 3/0268 422/502 |
| 7,402,440 B2 | 7/2008 | Wilmer et al. | |
| 8,071,049 B2 | 12/2011 | Koltay et al. | |
| 9,067,051 B2 | 6/2015 | Loth et al. | |
| 10,058,859 B2* | 8/2018 | Gehrig | B01L 3/022 |
| 2008/0156117 A1* | 7/2008 | Londo | B01L 3/0227 73/864.14 |
| 2008/0240898 A1 | 10/2008 | Manz et al. | |
| 2012/0291872 A1* | 11/2012 | Brady | G01N 35/1065 137/3 |
| 2013/0280143 A1* | 10/2013 | Zucchelli | B25J 9/1697 422/501 |
| 2013/0327787 A1 | 12/2013 | Koltay et al. | |
| 2016/0067705 A1* | 3/2016 | Gehrig | B01L 3/022 73/864.11 |
| 2017/0102403 A1* | 4/2017 | Zumbach | F04B 9/00 |
| 2017/0173576 A1* | 6/2017 | Natsume | B01L 3/0237 |
| 2018/0246134 A1* | 8/2018 | LaChance | B01L 3/021 |

FOREIGN PATENT DOCUMENTS

| | | |
|---|---|---|
| DE | 10 2013 006 227 A1 | 10/2014 |
| DE | 20 2014 006 241 U1 | 12/2015 |
| EP | 1 449 586 A1 | 8/2004 |
| WO | 2006/076957 A1 | 7/2006 |
| WO | 2014/166635 A1 | 10/2014 |

OTHER PUBLICATIONS

A. Madjarov, W. Streule, P. Prokopp, A. Ernst, R. Zengerle and P. Koltay; Nanoliter Dispensing on Pipetting Workstations by Disposable Pipjet-Tips; Actuator 2012, 13th International Conference on New Actuators, Bremen, Germany, Jun. 18-20, 2012, pp. 430-433.
Dr.-Ing. Wolfgang Streule, Gesundheit, Pipejettip, Microtec Südwest, Actuator 2012, 13th International Conference on New Actuators, Bremen, Germany, Jun. 18-20, 2012, p. 1-16.
Streule, W. [U. A.]: Pipejet: A Simple Disposable Dispenser for the Nano—and Microliter Range. In: J. Lab. Autom., vol. 9, 2004, NR. 5, S. 300-306. ISSN 1535-5535.
Rose, D.: Microdispensing Technologies in Drug Discovery. In: Drug Discover Today, vol. 4, 1999, NR. 9, S. 411-419.—ISSN 1359-6446.

* cited by examiner

PIPETTING APPARATUS FOR ASPIRATING AND DISPENSING LIQUIDS

CROSS-REFERENCE TO RELATED APPLICATION

The present U.S. application is related to and claims priority of German utility model application 20 2016 004 140.2 of Jul. 5, 2016. The aforementioned German application is fully incorporated by reference into the present application.

BACKGROUND OF THE INVENTION

Field of the Invention

The Invention relates to a pipetting apparatus for aspirating and dispensing liquids.

Description of Related Art

Pipetting apparatus of this kind are used inter alia, in the field of the automatic handling of liquid samples. They are frequently constituents of automated pipetting machines or pipetting robots.

In such a pipetting apparatus, a pipetting unit is moved into different operating positions by means of a positioning device. The positioning device can be an X/Y/Z displacement device. It can also be the arm of a robot which can be moved back and forth largely freely in space. The prior art provides various suggestions in this regard.

In pipetting apparatus as are used in the present case, vessels are used to take up and dispense liquid to be transferred. Usually, these are pipette tips which are picked up from a store of tips at a pick-up position and are coupled to coupling points of the pipetting unit. Then, the pipetting unit is moved into a liquid take-up position by means of the positioning device. In order to take up the liquid into the pipette tips, in other words for aspiration, the mouth openings of the pipette tips are dipped into liquid in corresponding storage vessels, for example, the wells of a microtiter plate. The liquid is taken up through the action of a displacement unit or a plurality of displacement units in the pipetting unit.

In conventional pipetting apparatus for relatively large volumes to be dispensed, for example, in the range of microliters, the pipetting unit is moved, after liquid has been taken up, into a liquid dispensing position by means of the positioning device. There, again by means of the action of the displacement unit or displacement units, the desired liquid volume is dispensed from the respective pipette tip into a target vessel. In this case, too, this can again be wells of a microtiter plate.

Metered dispensing operations for dispensing relatively small minimum volumes of liquid to be dispensed, for example, a subvolume of a drop down into the nanoliter range, cannot be realized in this way.

International Patent Application Publication WO 2014/166635 A1 and corresponding U.S. Patent Application Publication 2016/0067705 disclose a pipetting apparatus constructed in accordance with practice, having a micrometering unit for dispensing small minimum volumes of liquid to be dispensed, wherein the micrometering unit is advantageously embodied in a modular manner as a unit that is separate from the pipetting unit but is able to be fastened thereto in a readily releasable manner. The pipetting apparatus with a pipetting unit is provided in a conventional manner. By means of a coupling device, the micrometering unit is held in a releasable manner and optionally carried along.

A metering system having a device for releasably fastening a tool is disclosed in a further prior art (European Patent Application Publication EP 1 449 586 A1 and corresponding U.S. Pat. No. 7,402,440). Is in this case, the tool is either a metering tool having a metering head with at least one seat for fastening at least one pipette tip, or a syringe or a gripping tool. In any case, the metering system has a device for actuating the tool. Furthermore, the metering system has a device for controlling the tool. A programmable electronic storage device is carried along directly on the tool. If the tool is fastened releasably to the metering apparatus, a device serves to bring both the storage device of the tool and the metering system or the device for controlling the electrical connection into contact with one another. To this end, the device for making contact has a spring contact strip and a contact strip, which are embodied as a flat plug system. A plug system having a fastening peg on the tool serves as a device for releasable fastening. Therefore, the tool can be mounted on the metering apparatus only in an axial orientation and an exact position.

The above-described metering system has devices for making electrical contact for conventional, driven and non-independent pipetting systems which are assembled in a linear movement.

SUMMARY OF THE INVENTION

Proceeding from the prior art mentioned above, the primary object of the present invention is to specify improved making of electrical contact for a pipetting apparatus having a pipetting unit and a micrometering unit. Similarly, the process of this making of electrical contact is intended to be improved.

The subject matter of the invention is a pipetting apparatus comprising a pipetting unit with an interchangeable vessel that receives a liquid to be transferred, a holder for the pipetting unit, a positioning device for the pipetting unit, a micrometering unit, and an electronic control device, wherein the micrometering unit is embodied separately from the pipetting unit and has a separate electronic control unit, wherein the micrometering unit is optionally couplable to the pipetting unit in a precisely defined relative position, wherein the pipetting unit has a coupling device and the micrometering unit has a counterpart coupling device that matches the coupling device for the purpose of coupling, and wherein the coupling device and/or the counterpart coupling device is/are switchable, wherein the holder or the micrometering unit has a contact device with at least one electrical contact element, wherein the micrometering unit or the holder has a counterpart contact device, matching the contact device, with at least one counterpart electrical contact element for making electrical contact with the contact element, wherein the contact device is arranged on the holder or on the micrometering device so as to be movable from a contact position into a disconnected position and vice versa, wherein, when the at least one contact element is in an electrical contact connection with the at least one counterpart contact element, the micrometering unit is electrically connected to the control device of the pipetting apparatus.

A precondition for the invention is first of all that the micrometering unit is embodied as a unit separate from the pipetting unit. This means that the pipetting unit can be handled and used in different relevant operating positions, in particular in the pipette-tip pick-up position, the liquid take-up position, but also preferably in the pipette-tip discard position and optionally the ejection position for residual liquid, like a conventional pipetting unit of a pipetting apparatus without a micrometering unit.

In contrast, the micrometering unit is coupled to the pipetting unit, specifically in a precisely defined relative position with respect to the pipetting unit, when it is used, namely in the liquid dispensing position.

The pipetting apparatus has a pipetting unit without a micrometering unit where the micrometering unit is not required. It is converted into a pipetting apparatus with a micrometering unit where this is required, namely during liquid dispensing.

In principle, it is possible for the micrometering unit to be fitted permanently in a fixed position in the pipetting apparatus and for the respective receiving vessel for the liquid to be transferred to be moved relative to the micrometering unit in the pipetting apparatus. In this case, the pipetting unit is coupled to the micrometering unit in order to reach the liquid dispensing position.

In a preferred embodiment of the pipetting apparatus according to the invention, the pipetting unit can be moved freely together with its micrometering unit for liquid dispensing, for example, over different microtiter plates which are situated in different locations and for their part do not need to be moved.

If the micrometering unit is required for liquid dispensing, then use is made according to the invention of devices for making contact, which are arranged for the one part on or in the micrometering unit and for the other part on or in the holder on the pipetting unit, in order to also bring the micrometering unit into electrical contact with the pipetting unit when the micrometering unit is mechanically coupled to the pipetting unit. The holder is otherwise connected to the pipetting apparatus such that a power supply for the micrometering unit is provided via the device for making contact on or in the holder.

It goes without saying that the electrical connection of the micrometering unit to the pipetting apparatus is otherwise permanent throughout the pipetting operation. If the micrometering unit is no longer required, the connection is released in the reverse order analogously to the operation of making electrical contact, such that the micrometering unit can be uncoupled from the pipetting unit.

Devices for making electrical contact are, as described above, arranged in each case on or in the micrometering unit and holder. A contact device on the holder has at least one contact element. A further counterpart contact device, corresponding thereto, on the micrometering unit has a counterpart contact element. The contact device is arranged on the holder in a movable manner and the movement can be switchable. The micrometering unit enters into a releasable electrical connection with the rest of the pipetting apparatus via the holder, wherein the connection is switched or released via the movability of the contact device. The electrical connection is, as a result, established independently of the mechanical coupling, preferably after the coupling.

According to the invention, it is preferred for the contact device to be located on the holder for the pipetting unit and thus to be able to be moved, together with the pipetting unit, into spatially different operating positions by means of the positioning device. In this preferred embodiment of the pipetting apparatus according to the invention, the counterpart contact device is located on the micrometering unit.

However, it is also possible in principle for a reverse assignment of the contact device and counterpart contact device to be realized. It is usually the case, however, that there is less space in the micrometering unit than on the holder, and so preference is given to attaching the device that takes up less space to the micrometering unit than to the holder.

In the discussion in the claims and in the description, expressions such as "on the holder and on the micrometering unit, respectively" or "on the micrometering unit or on the holder" should be understood as meaning that the initially selected variant for this assignment continues to apply, i.e., it is subsequently clear, from the initially made assignment, where the contact device is located and where the counterpart contact device is located.

In a preferred embodiment, the contact device can be switched by a switching device preferably arranged in the micrometering unit, said switching device for its part advantageously being driven by a control track in the micrometering unit. A drive present in the micrometering unit can be used in order to switch the electrical connection.

In another embodiment, the contact device can be driven by an actuator in a manner controlled by the control unit of the pipetting apparatus, independently of other functional processes. The contact device with the at least one contact element moves, at best before the micrometering unit is coupled to the pipetting unit, to a travel limit located at a distance from the counterpart contact device and in the direction of the counterpart contact device during or after coupling, wherein, as a result, the contact and counterpart contact elements then come into engagement and the electrical connection is produced. Preferably, the actuator is arranged on the holder.

As already stated above, the teaching of the invention is realizable in a pipetting apparatus, in which the micrometering unit is located in a fixed position in the pipetting apparatus and the receiving vessels for liquid to be transferred, for example, in the form of a microtiter plate, are moved in the pipetting apparatus relative to the micrometering unit arranged in a fixed position. In this variant of the pipetting apparatus according to the invention, the pipetting unit is coupled to the micrometering unit located in a fixed position, in order that liquid dispensing operations can be carried out.

According to preferred teaching of the invention, however, provision is made for the micrometering unit coupled to the pipetting unit to be able to be moved, together with the pipetting unit, into spatially different operating positions by means of the positioning device.

In addition, in particular with regard to the preferred configuration of the pipetting apparatus that was discussed above, reference is made to previously mentioned International Patent Application Publication WO 2014/166635 A1 and corresponding U.S. Patent Application Publication 2016/0067705, which is hereby incorporated by reference. All of the proposals, suggestions and design variants therein can also be applied in the present invention.

The subject of the invention is also a method for operating a pipetting apparatus of the type in question, in particular a pipetting apparatus according to one or more of the apparatus claims.

This method has at least the following method steps:

a) The holder having a movable contact device with at least one contact element is moved, by means of the positioning device, from an end position on the micrometering unit set down at a particular position, said micrometering unit having a counterpart contact device with at least one counterpart contact element, into a starting position of the coupling operation, in which the contact device and the counterpart contact device are still spatially at a distance from one another.

b) The holder is moved further by means of the positioning device into an intermediate position, in which the contact device is only still spaced apart from the counterpart contact device substantially one-dimensionally, such that the at least one contact element and the at least one counterpart contact element are spaced apart from one another.

c) The holder is moved further by means of the positioning device into a contact position, in which the at least one contact element and the at least one counterpart contact element enter into an electrical connection.

d) In order to release the electrical connection, the holder is moved by means of the positioning device into an end position at a distance from the micrometering unit, wherein the method steps c), b), a) are executed in that order.

During this process, it is ensured that the mechanical coupling of the holder to the micrometering unit takes place without collision. The method steps furthermore ensure that the contact elements are also not damaged during repeated coupling and remain reliable in operation.

In a preferred method step, before method step b), an actuating device, arranged on the micrometering unit, for the vessel is used to extend a locking device, likewise arranged on the micrometering unit, such that the counterpart contact device cannot enter into an electrical connection with the contact device and the at least one contact element is not damaged by subsequent relative movements.

In method step c), the actuating device of the micrometering unit can retract the locking device. In a manner driven by the locking device, a protective device which is arranged on the holder and on which the at least one contact element is arranged is moved into a connecting position. A separate actuator is not necessary for this purpose. By way of this movement, the at least one contact element and the at least one counterpart contact element enter into an electrical connection.

In a preferred method variant, in method step b), the movement is one-dimensional or two-dimensional. Depending on the embodiment of the contact elements, a particular movement is advantageous. In the case of punctiform contact, a vertical movement suffices. In the case of planar contact, a small horizontal movement should additionally take place for an optimal contact connection during compression.

According to a preferred variant of the described method, in method step a), the movement can be two-dimensional or three-dimensional.

It is also the case for the method according to the invention that it can be carried out with a micrometering unit located in a fixed position in the pipetting apparatus. However, it is also the case for the method according to the invention that a preferred embodiment of the method according to the invention proceeds from the fact that the micrometering unit coupled to the pipetting unit can be moved, together with the pipetting unit, into spatially different operating positions by means of the positioning device between method steps c) and d). According to preferred teaching, in order to dispense the liquid to be transferred from the vessel, between method steps c) and d), the micrometering unit with the pipetting unit is accordingly moved into one or more dispensing positions over one or more target vessels.

Explanation of the advantages of the invention and of preferred configurations and developments is made below in conjunction with an explanation of preferred illustrative embodiments with reference to the accompanying drawings.

DETAILED DESCRIPTION OF THE INVENTION

The subject of the invention is a pipetting apparatus 1 having a pipetting unit 2. Reference is also made here to the prior art in International Patent Application Publication WO 2014/166635 A1 and corresponding U.S. Patent Application Publication 2016/0067705, which disclose a pipetting apparatus 1 of the type discussed herein overall and in great detail. The entire disclosure of the U.S. Patent Application Publication 2016/0067705 is incorporated by reference into the present application since all of the design and engineering configurations therein are also implementable in the pipetting apparatus 1 of the present application.

Figure 1:
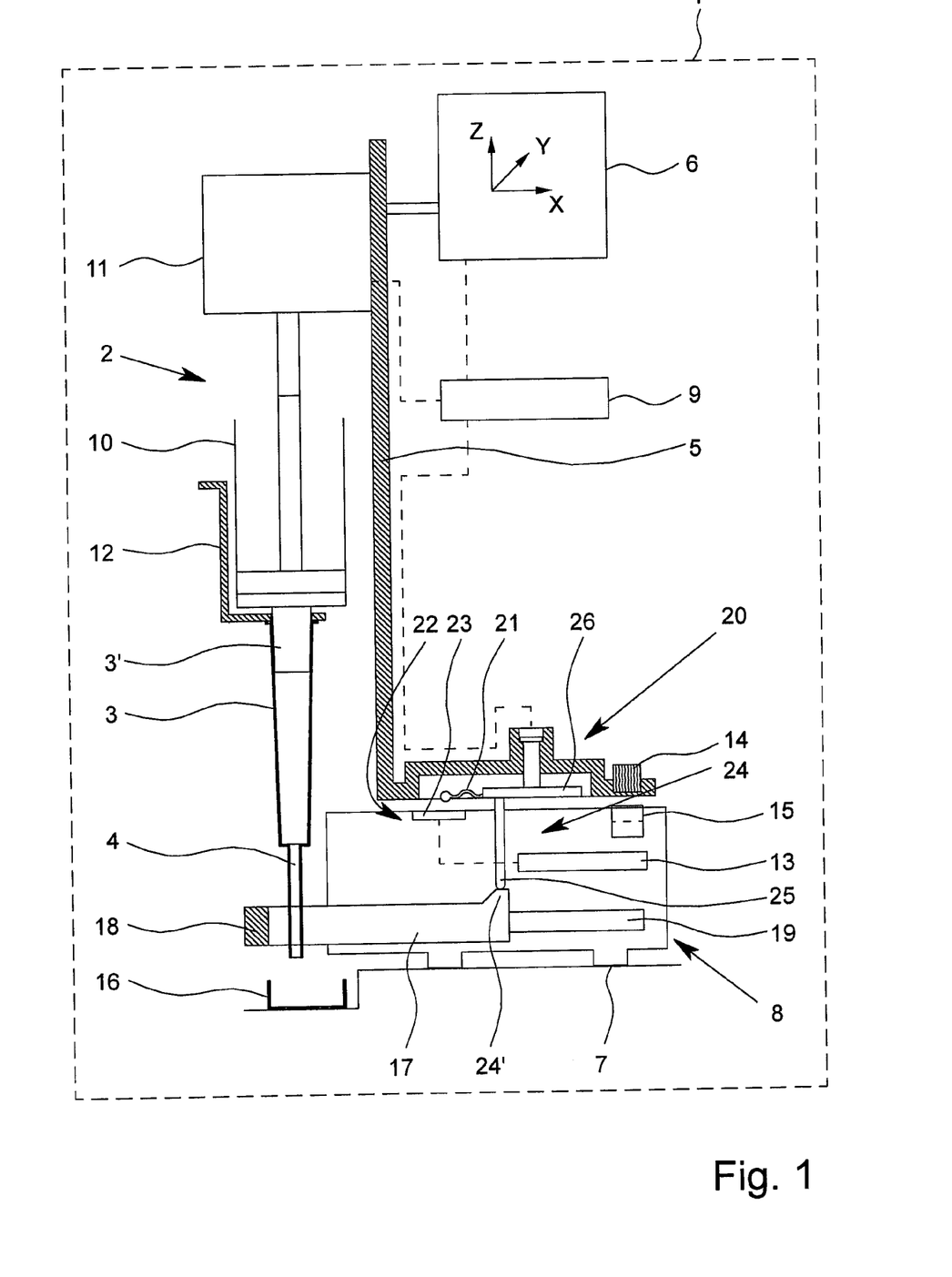
FIG. 1 is a a schematic side view of a preferred exemplary embodiment of a pipetting apparatus according to the invention.

FIG. 1 shows a complete illustration of a preferred exemplary embodiment of a pipetting apparatus according to the invention, the structure of which is first of all intended to be explained in detail with reference to FIG. 1.

The pipetting apparatus 1 which is illustrated in FIG. 1 by way of a dashed-line frame, first of all has a pipetting unit 2, which for its part has a vessel 3 receiving a liquid to be transferred. The vessel 3 is preferably embodied in the form of a pipette tip 3 and attached in an interchangeable manner to the pipetting unit 1. The scope of the invention also includes a pipetting apparatus 1 in the form of a multi-duct pipetting apparatus, in which a plurality of vessels 3 are then located on the pipetting unit 1.

Preferably, the vessel 3 is a pipette tip which has an elastically deformable expulsion end 4. Reference may be made here to the explanation of this vessel 3 in detail in U.S. Patent Application Publication 2016/0067705.

Furthermore, the pipetting apparatus 1 has a holder 5 for the pipetting unit 2, to which the pipetting unit 2 is attached. By means of a positioning device 6, which is illustrated as an X/Y/Z coordinate device in FIG. 1, the pipetting unit 2 can be moved in space, in this case in conjunction with the holder 5.

At the bottom right of FIG. 1, a micrometering unit 8 set down locally on a set-down platform 7 there can be seen.

The entire pipetting apparatus 1 is furthermore completed by an electronic control device 9, by way of which all of the processes of the pipetting apparatus 1 are controllable as desired. Dashed lines in FIG. 1 indicate where transmission means for control commands, power supply and/or data are provided between the individual components of the pipetting apparatus 1. It is of course possible for much more in the way of transmission means to be provided, but this will not be discussed in detail here.

The vessel 3 embodied as a pipette tip is connected interchangeably to the pipetting unit 2 at a coupling point 3'. Such a coupling point 3' is typically configured in the form of a pipette shaft, and in this regard, too, reference is made to U.S. Patent Application Publication 2016/0067705.

The pipetting unit 1 has a displacement unit 10 that is connected in terms of flow to the coupling point 3' and to the vessel 3 attached thereto. For the arrangement, configuration and function thereof, reference is again made to U.S. Patent Application Publication 2016/0067705. The displacement unit 10 is assigned a drive 11 and a tip ejection apparatus 12 for the vessel 3 in the form of a pipette tip.

Figure 2:
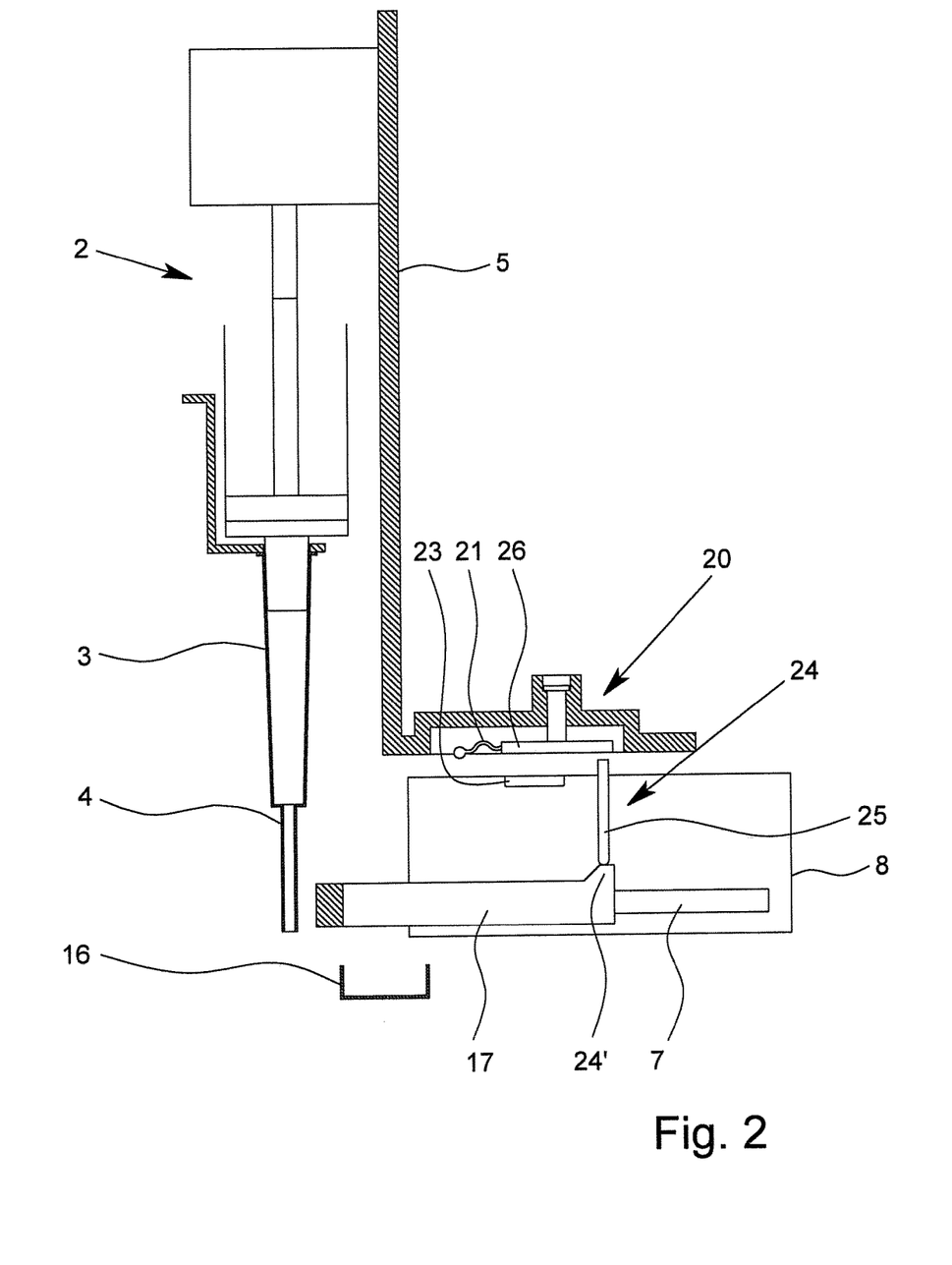
FIG. 2 shows, proceeding from the illustration in FIG. 1, but simplified, the pipetting apparatus from FIG. 1, the pipetting unit having been moved up to the locally set-down micrometering unit.

The drawing in FIG. 2 shows that, in the pipetting apparatus 1, the micrometering unit 8 is embodied separately from the pipetting unit 2. These are two units that are spatially separable from one another and are able to be handled independently of one another. The micrometering unit 8 itself also has an electronic control unit 13.

Figure 4:
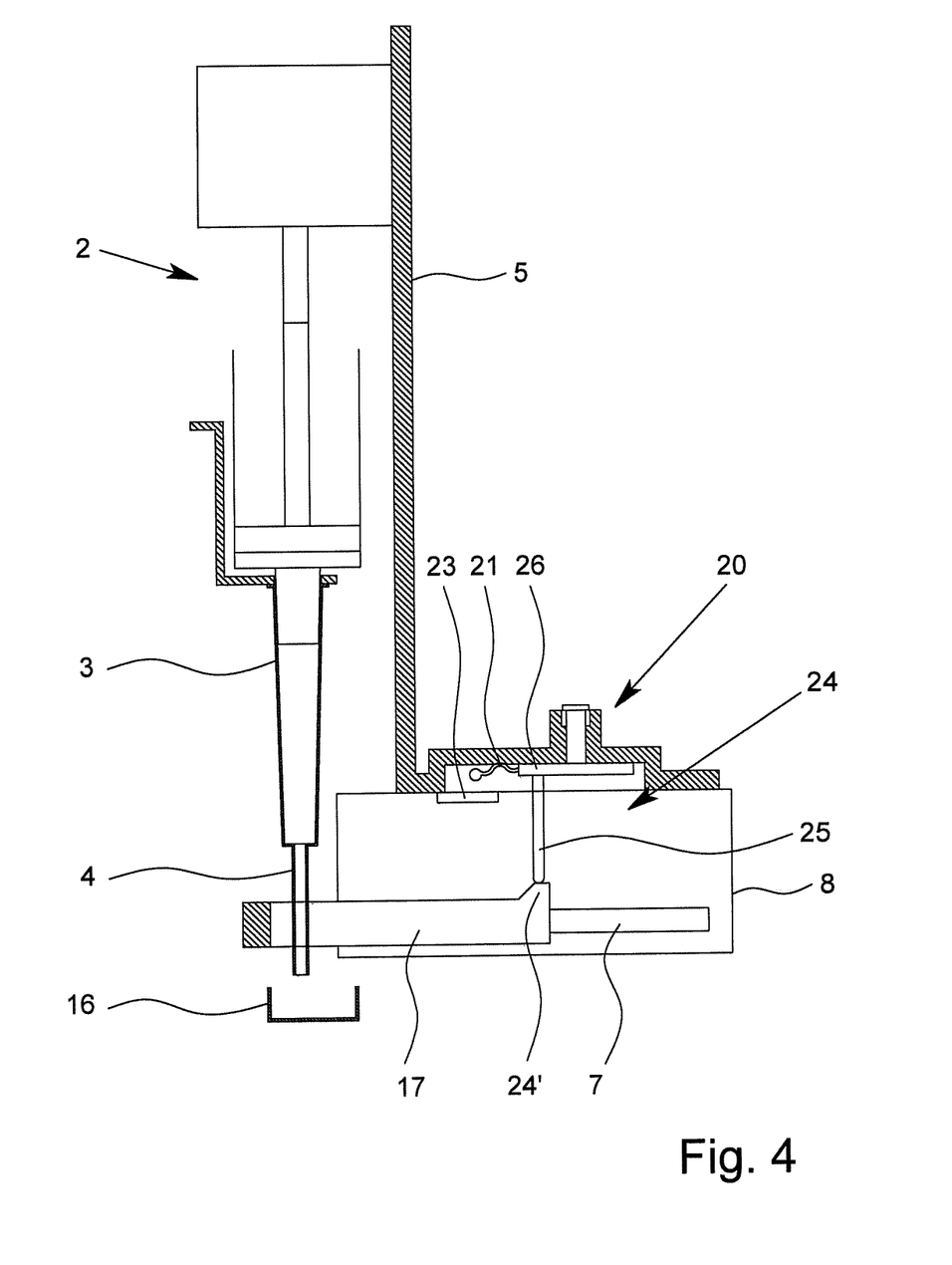
FIG. 4 shows the pipetting unit, proceeding from the illustration in FIG. 3, now lowered vertically onto the micrometering unit and coupled or able to be coupled thereto.
Figure 5:
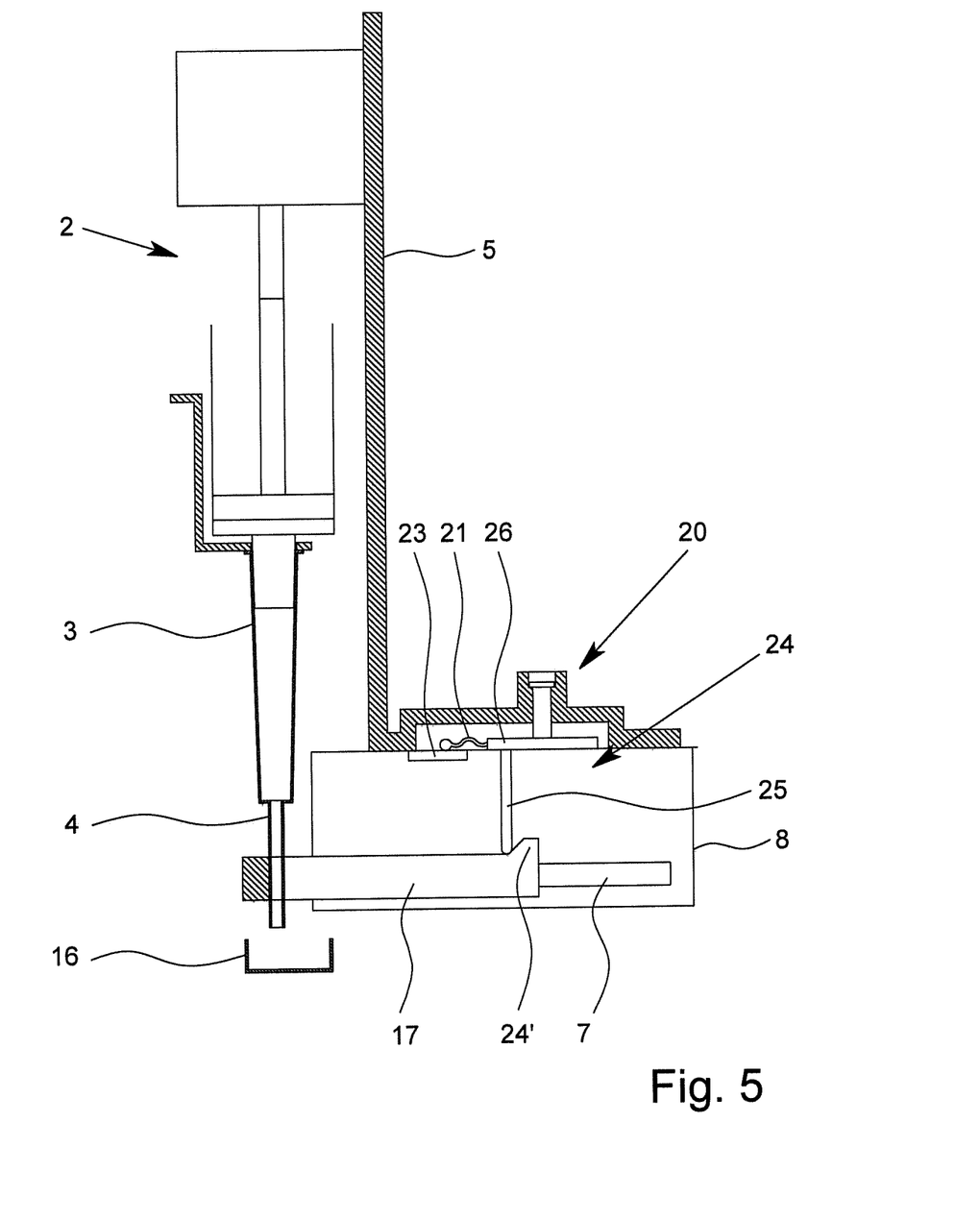
FIG. 5 shows, proceeding from the illustration in FIG. 4, the electrical contact device electrically coupled to the counterpart electrical contact device.

By means of the positioning device 6, the pipetting unit 2 can be moved into different operating positions. In this regard, FIG. 1 shows a position of the pipetting unit 2 close to the micrometering unit 8, which is still located on the set-down platform 7, i.e., shortly before reaching or shortly after leaving a coupling position. The coupling position itself is shown in FIG. 4 and FIG. 5. Otherwise, reference is made, here too, to U.S. Patent Application Publication 2016/0067705.

In the present case, a pipetting apparatus 1 according to a preferred embodiment of the invention is illustrated and described, namely a pipetting apparatus 1 in which the micrometering unit 8 is able to be moved, together with the pipetting unit 2, into spatially different operating positions by means of the positioning device 6.

Regardless thereof, it is also possible to understand from the following explanations of the preferred embodiment of the invention that the present invention is also able to be realized in a pipetting apparatus 1 in which the micrometering unit 8 is permanently positioned in a fixed position in the system of the pipetting apparatus 1 and the pipetting unit 2 can be coupled, as required, to the micrometering unit 8 located in a fixed position. Reference may be made here to the statements given with respect to this variant of the invention in the general part of the description. All aspects of the invention which are not expressly restricted to the micrometering unit 8 that is movable, as required, with the pipetting unit 2 are also able to be applied in a pipetting apparatus 1 having a micrometering unit 8 arranged permanently in a fixed position.

What is important for the invention is, first of all, that the micrometering unit 8 is optionally able to be coupled to the pipetting unit 2 in a precisely defined relative position. In the preferred variant of the invention, this takes place first of all when the pipetting unit 2 "retrieves" the micrometering unit 8 at the set-down platform 7. The set-down platform 7 offers a deliberately provided, defined space in the pipetting apparatus 1 for setting down the micrometering unit 8 when it is not in use. The set-down platform 7 is expediently positioned in a fixed position in the pipetting apparatus 1. This is all explained in the abovementioned citation.

In order to couple the pipetting unit 2 to the micrometering unit 8, the pipetting unit 2 has a coupling device 14, while the micrometering unit 8 has a counterpart coupling device 15 that matches the coupling device 14. The coupling device 14 and/or the counterpart coupling device 15 is/are switchable. As a result of the coupling device 14 and/or the counterpart coupling device 15 being switched, the micrometering unit 8 is optionally able to be coupled to the pipetting unit 2 or uncoupled from the pipetting unit 2. The advantages of this construction of the pipetting apparatus 1 have been explained in detail in the prior art discussed above, to which reference may be made here. For the configuration of the coupling device 14 and of the counterpart coupling device 15 in different variants, reference is likewise made to the abovementioned U.S. Patent Application Publication 2016/0067705.

Preferably, it is also the case for the teaching of the present invention that the counterpart coupling device 15 is embodied actively as a switched magnetic coupling, while the coupling device 14 is embodied passively as a counterpart made of ferromagnetic material.

As explained in detail in U.S. Patent Application Publication 2016/0067705, provision is also made in the present pipetting apparatus 1 for the micrometering unit 8 coupled to the pipetting unit 2 to be able to be moved, together with the pipetting unit 2, into spatially different operating positions by means of the positioning device 6, as long as the micrometering unit 8 is required in the respective operating position for the respective phase of operation of the pipetting apparatus 1. If it is not required, the micrometering unit 8 can remain on the set-down platform 7, and only the pipetting unit 2 is moved.

The present case relates to the making of electrical contact between the micrometering unit 8 for the one part and the rest of the pipetting apparatus 1 for the other part, in particular also between the micrometering unit 8 with the control unit 13 thereof and the control device 9 of the pipetting apparatus 1.

In accordance with the prior art in U.S. Patent Application Publication 2016/0067705, the exemplary embodiment in FIG. 1 of the drawing shows a receiving vessel 16 at the bottom, beneath the expulsion end 4 of the vessel 3 embodied as a pipette tip on the pipetting unit 2, it being possible for the receiving vessel 16 to be a well of a microtiter plate, for example. The transfer of liquid to be transferred from the vessel 3 into the receiving vessel 16 takes place in that the expulsion end 4, configured as an elastically deformable tube, of the pipette tip 3 is radially subjected to a back-and-forth movement of an actuating device 17 in the micrometering unit 8, such that it is deformed. As a result, liquid is dispensed in the form of droplets from the mouth of the expulsion end 4 into the receiving vessel 16.

In order to fix the expulsion end 4, a clamping jaw 18 or the like for the expulsion end 4 of the pipette tip 3 is additionally provided on the micrometering unit 8. The clamping jaw 18 is driven by means of an actuating device 17 and an actuator 19. With regard to this manner of operation of the micrometering unit 8, too, reference is made to U.S. Patent Application Publication 2016/0067705.

In the variant of the pipetting apparatus 1 with a micrometering unit 8 arranged permanently in a fixed position, care has to be taken in the pipetting apparatus 1 that the receiving vessel 16, i.e., in particular a microtiter plate or the like, can be shifted relative to the micrometering unit 8 in the pipetting apparatus 1, such that different receiving vessels 16 can be positioned under the expulsion end 4 of the vessel 3.

In the illustrated and preferred exemplary embodiment of the pipetting apparatus 1 according to the invention, however, the micrometering unit 8 is able to be moved, together with the pipetting unit 2, into different operating positions, when this is required.

In order to establish electrical contact between the holder 5 and the micrometering unit 8, provision is made for the holder 5 to have a contact device 20 with at least one electrical contact element 21. The illustrated exemplary embodiment shows the contact device 20 according to the preferred teaching on the holder 5. In principle, the contact device 20 could also be arranged on the micrometering unit 8, however.

The at least one contact element 21 of the contact device 20 is embodied as an inherently resilient contact finger in the illustrated and preferred exemplary embodiment. This is a preferred example but should not be understood as being exhaustive. Further preferred examples of contact elements are a resiliently mounted, i.e., spring-loaded contact finger or a resiliently mounted or inherently resilient contact pin.

In the illustrated and preferred exemplary embodiment, the micrometering unit 8 has a counterpart contact device 22 that matches the contact device 20 and has at least one counterpart electrical contact element 23 for making electrical contact with the contact element 21. The statement regarding the reverse arrangement that was already made above for the contact device 20 applies here, too, and so the counterpart contact device 22 can be arranged on the holder 5 rather than on the micrometering unit 8.

In each case, a contact element 21 and a counterpart contact element 23 are illustrated. However, it is quite possible or even preferred for the contact device 20 and the counterpart contact device 22 each to have a plurality of elements assigned to one another. These are preferably arranged in the manner of a matrix.

The number of contact elements 21 and counterpart contact elements 23 and the arrangement thereof depend on what is intended to be electrically transmitted via the contact device 20 and counterpart contact device 22. The charging current for a rechargeable battery in the micrometering unit 8 and a multiplicity of connections which serve to the control the pipetting apparatus 1 with its constituents come into consideration. In any case, at least one electrical contact element 21 of the contact device 20 is connected to the control device 9 of the pipetting apparatus 1.

A look at the further figures, namely in particular FIGS. 2 to 5, shows that, according to the teaching of the invention, the contact device 20 is arranged on the holder 5 (this being the variant illustrated in the drawings; alternatively on the micrometering unit 8) so as to be movable from a contact position into a disconnected position and vice versa. In FIG. 2, the contact device 20 is in the contact position but is not in contact with the counterpart contact device 22; the same goes for FIG. 3. In FIG. 4, the contact device 20 is in the disconnected position, and in FIG. 5, the contact device 20 is in the contact position but is now in contact with the counterpart contact device 22.

When the at least one contact element 20 is in an electrical contact connection with the at least one counterpart contact element 23, the micrometering unit 8 is otherwise electrically connected to the pipetting apparatus 1, specifically preferably also in terms of control to the control device 9 of the pipetting apparatus 1. This state is shown in FIG. 5, because said Figure reveals that not only is the contact device 20 in the contact position but the holder 5 is also in the above-described relative position on the micrometering unit 8, such that the contact element 21, which can be seen here, makes electrical contact with the counterpart contact element 23 and thus establishes the electrical connection.

FIG. 1 reveals, by way of the electrical connections illustrated by way of dashed lines, how the contact element 21 of the contact device 20 is connected here to the control device 9 of the pipetting apparatus 1. Likewise illustrated by dashed lines is the fact that the counterpart contact element 23 in the micrometering unit 8 is in any case connected to the control unit 13 there. Other connections in the micrometering unit 8 are not indicated, but may be present, in particular for example, to the electromagnet of the counterpart coupling device 15 and to the actuator 19.

FIGS. 2 to 5 and the preceding description reveal the process when contact is made in the pipetting apparatus 1 according to the invention. In FIG. 2, the pipetting unit was moved with the holder and by means of the positioning device from an end position at the micrometering unit up to a start position, this illustrating method step a).

Figure 3:
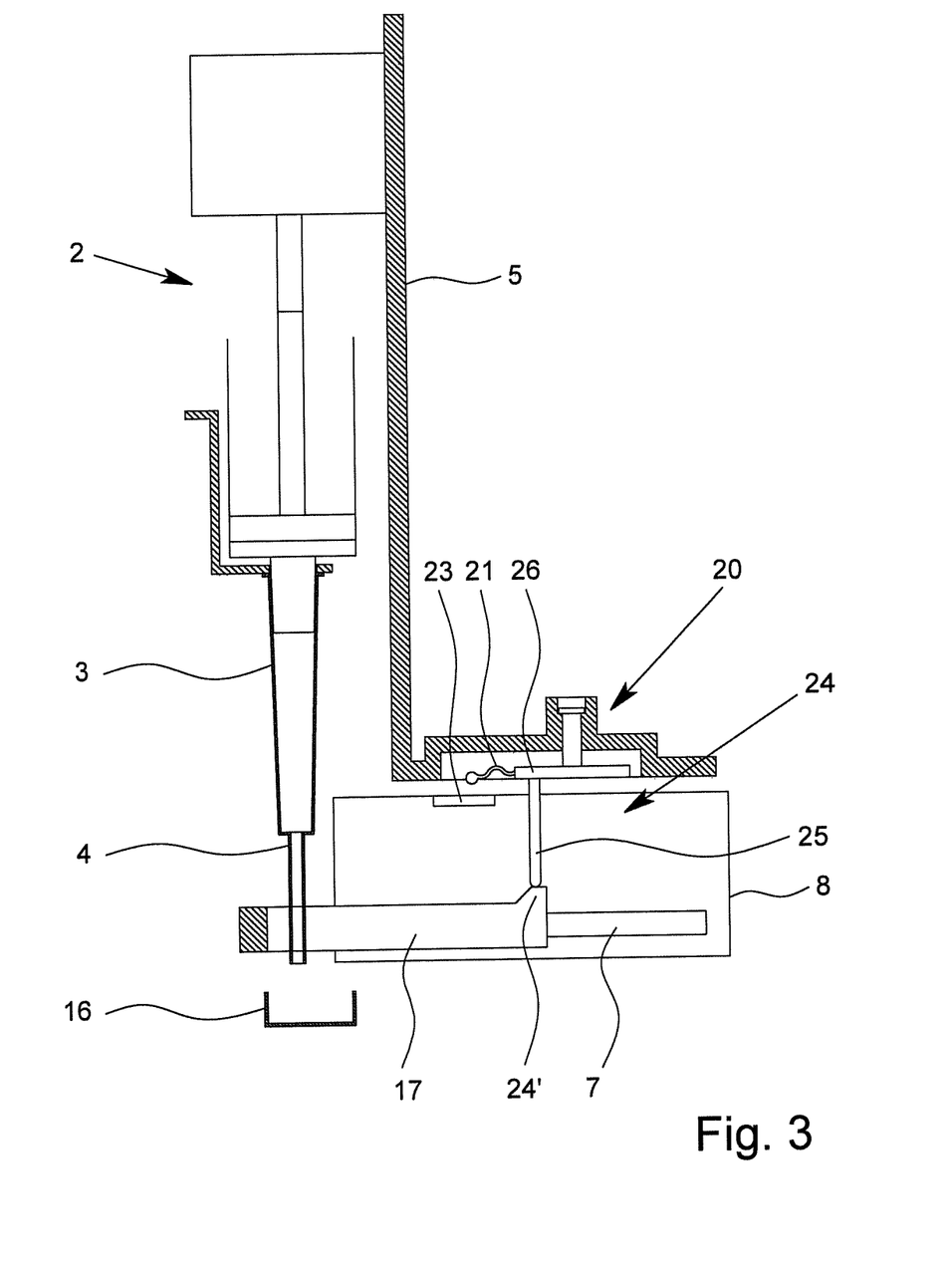
FIG. 3 shows, proceeding from FIG. 2, the pipetting unit moved to the right with respect to the micrometering unit, with the pipetting unit now in the correct relative position, in vertical orientation, with respect to the micrometering unit.

In a method step b), the holder is moved further into an intermediate position by means of the positioning device, as shown in FIG. 3. Here, spatially just before the coupling of the pipetting unit 2 and the micrometering unit 8 and preferably with the micrometering unit 8 coupled to the pipetting unit 2, the contact device 20 is able to be kept in the disconnected position up to a switching operation. Until the next method step c), the contact devices are only still spaced apart from one another substantially one-dimensionally.

FIG. 4 shows the holder for the micrometering unit 8 in a contact position, method step c), wherein the contact device 20 is in the disconnected position, although the pipetting unit 2 is or can be already coupled to the micrometering unit 8, specifically by the action of the coupling device 14 and the counterpart coupling device 15. As a result of the switching operation being triggered, the contact device 20 is then able to be moved into the contact position (transition from FIG. 4 to FIG. 5), in which the at least one electrical contact element 21 then makes contact with the at least one counterpart electrical contact element 23.

The illustrated and preferred exemplary embodiment shows a switching device 24 by way of which this switching operation is able to be triggered. In the illustrated exemplary embodiment, the switching device 24 according to the preferred teaching is located on the micrometering unit 8. In principle, it could also be arranged on the holder 5.

In the illustrated and preferred exemplary embodiment, the switching device 24 is coupled in terms of movement to the actuating device 17. The tightening of the clamping jaw 18 by means of the actuating device 17 is at the same time the operation which triggers the switching operation.

In the exemplary embodiment that is illustrated and to this extent preferred, provision is made in design terms for the switching device 24 on the micrometering unit 8 to have a movable locking bolt 25 which cooperates with the contact device 20 on the holder 5. In the exemplary embodiment that is specifically illustrated and preferred, this takes place via a control element 26 connected to the at least one contact element 21 of the contact device 20. Said control element 26 is in this case embodied as a kind of plate or disk which in this case carries the contact element 21 but is not itself involved in the making of contact.

In the illustrated and preferred exemplary embodiment, provision is made for the electrical connection from the contact element 21 into the rest of the pipetting apparatus 1, in particular to the control device 9, to take place through the control element 26, for example, through conductor tracks embedded there.

For the further explanation of preferred exemplary embodiments of the invention, reference is now made to the entire sequence of Figures from FIG. 1 to FIG. 5.

FIG. 2 shows that, in method step a), the pipetting unit 2 has been moved by means of the positioning device 6 toward the micrometering unit 8 located on the set-down platform 7 into the start position in a two-dimensional or three-dimensional movement, such that the holder 5 is a short distance above the micrometering unit 8. The clamping jaw 18 should be opened at the latest thereafter, before method step b), wherein the switching device 24 lifts the locking bolt 25 and moves it out of the micrometering unit 8.

From FIG. 2 to FIG. 3, the pipetting unit 2 has been moved one-dimensionally or two-dimensionally so far to the right relative to the micrometering unit 8 by way of the movement in method step b) that the pipette tip 3 has been arranged with its expulsion end 4 behind the clamping jaw 18 on the actuating device 17 of the micrometering device 8. With regard to the vertical orientation, the pipetting unit 2 is now in the correct relative position with respect to the micrometering unit 8. It has also been lowered a little with respect to the micrometering unit 8 such that the control element 26 of the contact device 20 just sits on the tip of the locking bolt 25 of the switching device 24.

In the transition from FIG. 3 to FIG. 4, the pipetting unit 2 has been fully lowered vertically onto the micrometering unit 8 by means of the positioning device 6 and coupling to the micrometering unit 8 by means of the coupling device 14 and counterpart coupling device 15, which are not shown in FIG. 4, has taken place. Regardless thereof, the contact element 21 of the contact device 20 has not yet made contact with the counterpart contact element 23 of the counterpart contact device 22 because the contact element 21 has not yet been able to move downward. It remains lifted by means of the control element 26, supported by the locking bolt 25 of the switching device 24.

At the transition from FIG. 4 to FIG. 5, it is possible to see that electrical contact is made in the pipetting apparatus 1 according to the invention independently of the mechanical or electromechanical or magnetomechanical coupling of the pipetting unit 2 to the micrometering unit 8. Electrical contact is made specifically by the triggering of a switching operation, by way of which the contact device 20 is movable from the disconnected position into the contact position. In the transition from FIG. 4 to FIG. 5, it is possible to see that the actuating device 17 has been displaced there toward the right in the drawing by means of the actuator 19, in order to position the clamping jaw 18 toward the right against the expulsion end 4 of the pipette tip 3. At the same time, the locking bolt 25 has been moved downward on the corresponding control track 24' in the micrometering unit 8 and has thus released the control element 26 with the contact element 21 for a corresponding movement downward into the contact position. The contact element 21 now touches the counterpart contact element 23 and the electrical contact connection is established.

The micrometering unit 8 coupled to the pipetting unit 2 according to FIG. 5 is now moved, together with the pipetting unit 2, into spatially different operating positions by means of the positioning device 6. Between method steps c) and d), the pipetting unit 2 is moved with the micrometering unit 8 into a dispensing position in order to dispense liquid from the vessel.

The uncoupling according to the invention of the making of electrical contact from the mechanical connection of the pipetting unit 2 to the micrometering unit 8 takes place in a method step d), wherein method steps c), b), a) take place in that order. The pipetting unit 2 with the holder 5 is then moved from the start position into an end position at a distance therefrom by means of the positioning device 6, and from there the process is started again.

This individualization according to the invention of the electrical connection has the advantage that the frequently very sensitive contact elements 21 are brought into contact with one another in the switching operation only in a precisely controlled positioning movement that is able to be planned perfectly in advance. During this operation, the mechanical connection of the pipetting unit 2 to the micrometering unit 8 has already been completed, and so no or at least only minimal displacements of the pipetting unit 2 and the micrometering unit 8 relative to one another can occur. The electrical contact connection is protected.

The exemplary embodiment illustrated in the drawing shows the generally expedient design whereby, in order to make electrical contact, the contact device 20 and the counterpart contact device 22 are movable relative to one another in a particular joining direction, and wherein the contact device 20, in particular the control element 26 with the contact element 21, is mounted on the holder 5 so as to be movable in the joining direction.

FIG. 1 reveals that, in this case, and according to preferred teaching, a further preferred assignment of particular directions of movement can be made, namely such that the coupling device 14 and the counterpart coupling device 15 for coupling the micrometering device 8 to the pipetting unit 2 are movable relative to one another in a particular joining direction, and that the joining direction for the movement of the contact device 20 and the counterpart contact device 22 corresponds to the joining direction for the movement of the coupling device 14 and the counterpart coupling device 15.

The exemplary embodiment illustrated does not show any additional spring elements or the like in the figures. Preferably, however, both the locking bolt 25 and the control element 26, which is embodied in this case as a plate or disk, can be subjected to a spring force counter to the joining-together direction of the components. By way of a resilient configuration or application of spring force, the movement of the component that is required in each case can be controlled in a targeted manner, this not being readily possible with a movement triggered solely by weight force.

Figure 7:
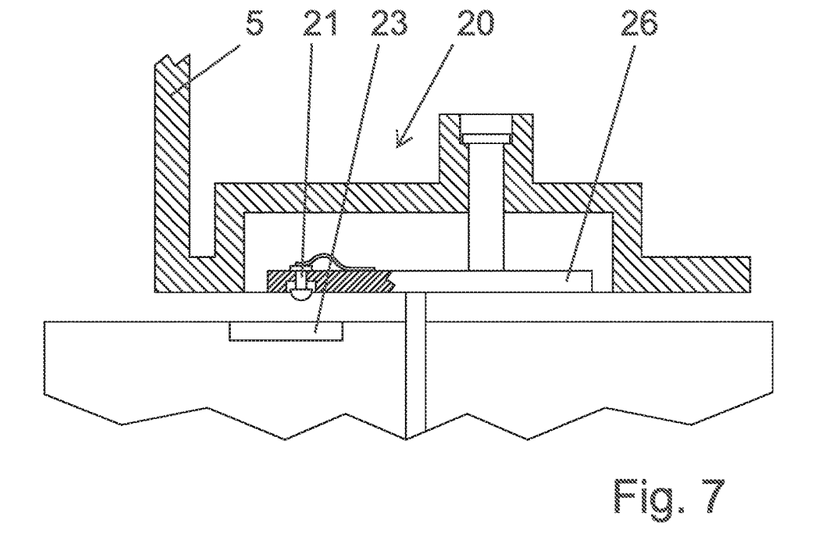
FIGS. 7 & 8 show an embodiment in which the electrical contact element is a spring-mounted contact pin, positions uncoupled and coupled, respectively to the counterpart electrical contact element.
Figure 8:
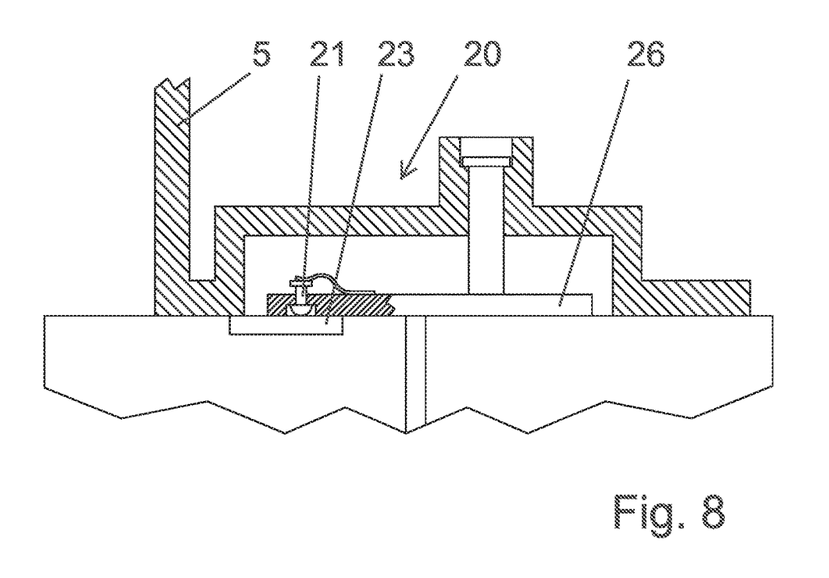

When pin-like components are used, a predominantly one-dimensional positioning movement against the respective counterpart is recommended. A spring-mounted contact pin 21 (FIGS. 7 & 8) or inherently resilient contact finger (FIGS. 4 & 5) occasionally has an advantage over a contact pin because, during the joining of the components that takes place substantially in one dimension, a certain lateral movement also takes place on the counterpart, this ensuring a better contact connection.

The design of the pipetting apparatus 1 illustrated in FIG. 1 is distinguished overall with regard to the micrometering unit 8 in that the control unit 13 of the micrometering unit 8 is connected in terms of control to the drive unit for the switching device 24, namely the actuator 19 of the actuating device 17, wherein the actuating device 17 and the actuator 19 are controllable from the control unit 13 of the micrometering unit 8. This is a preferred embodiment of the micrometering unit 8, which is in any case predominantly autonomous in terms of control.

An actuator 19 is preferably an electromotive actuator. In principle, however, it can also be an electromagnetic drive or a pneumatic or hydraulic drive.

Figure 6:
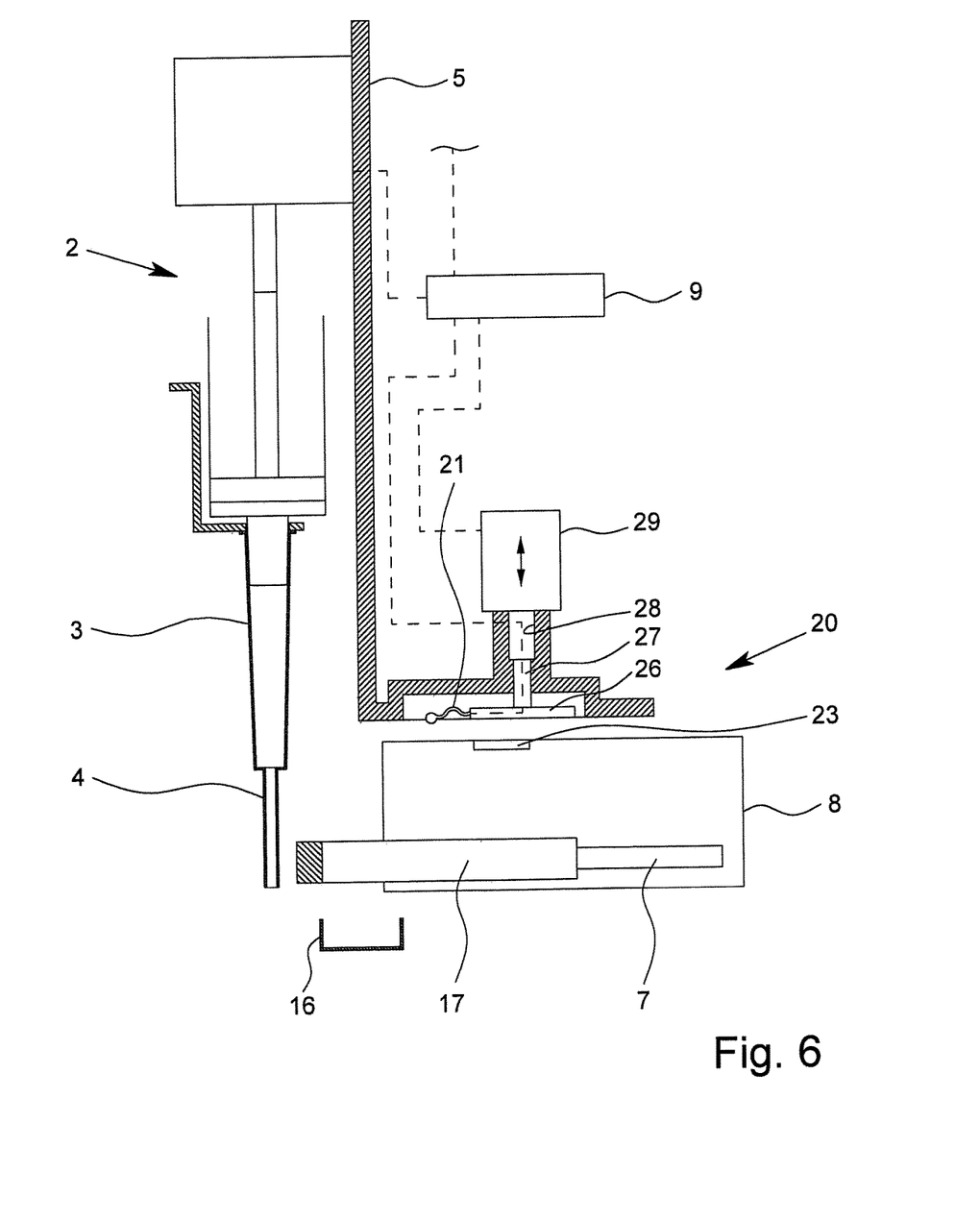
FIG. 6 shows an illustration corresponding to FIG. 2 of another exemplary embodiment with an actuator on the holder of the pipetting unit.

FIG. 6 shows the illustration of a further exemplary embodiment of a pipetting apparatus 1 according to the invention in a highly schematic illustration corresponding to FIG. 2. Identical components to those in FIG. 2 have the same reference signs. In this case, the dashed connecting lines from the control device 9 of the pipetting apparatus 1 to the various other components of the pipetting apparatus 1, and in particular also inside the control element 6 as far as the contact element 21 of the contact device 20 attached thereto, can be seen.

The illustrated control element 26 is in this case guided so as to be displaceable vertically upward and downward on the holder 5, as also in the exemplary embodiment in FIG. 1 to FIG. 5, by means of a shaft 27 in a sleeve-like guide 28 on the holder 5. As a result, the one-dimensional movement or displacement movement of the control element 26 on the holder 5 that is explained above is ensured.

In contrast to the exemplary embodiment illustrated in FIGS. 1 to 5, the vertical movement of the control element 26 of the contact device 20 for the purpose of moving the contact device 20 between the contact position and disconnected position is not initiated mechanically from the micrometering device 8 but directly from the holder 5 by means of an actuator 29 arranged there on the holder 5.

In FIG. 6, this actuator 29 and the upward and downward movement that is able to be triggered thereby are illustrated. The actuator 29 is preferably an electromagnetic drive, in particular in the form of a solenoid. However, it can also be some other drive of the pneumatic, hydraulic or electromotive type (linear drive). In the illustrated and preferred exemplary embodiment, the actuator 29 is not controlled by the control unit 13 of the micrometering unit 8 but directly by the central control device 9 of the pipetting apparatus 1. In the micrometering unit 8 itself, there are in this case no constituents of a switching device, rather the actuator 29 is provided on the holder 5.

The present description of the illustrative embodiments will not limit the scope of protection of the present invention. The scope of protection is determined exclusively by claims and also encompasses equivalents of the features referred to in the claims.

What is claimed is:

1. A pipetting apparatus comprising:
    a pipetting unit,
    a pipetting vessel detachably mountable on the pipetting unit at a coupling point for receiving a liquid from a storage vessel and dispensing the liquid into a receiving vessel,
    a displacement unit arranged in the pipetting unit for taking up of liquid from the storage vessel and for dispensing the liquid from the pipetting vessel,
    a holder to which the pipetting unit is mounted, the holder being mounted for movement,
    a positioning device connected to the holder for moving the pipetting unit in conjunction with the holder,
    a micrometering unit located on a platform and to which the holder is detachably connectable in a precisely defined relative position, and
    an electronic control device having transmission means for electronically providing control commands, power supply and data between the electronic control device and individual components of the pipetting apparatus,
    an electronic control unit for the micrometering unit, the electronic control unit being separate from said electronic control device,
    wherein the holder has a coupling device and the micrometering unit has a counterpart coupling device that matches the coupling device for coupling of the pipetting unit, via the holder, to the micrometering unit, and
    wherein at least one of the coupling device and the counterpart coupling device is switchable between a coupled position and a decoupled position for coupling the micrometering unit to the pipetting unit and uncoupling the micrometering unit from the pipetting unit,
    wherein one of the holder or the micrometering unit has a contact device with at least one electrical contact element,
    wherein the other of micrometering unit or the holder has a counterpart contact device, matching the contact device, the counterpart contact device being provided with at least one counterpart electrical contact element for making electrical contact with the contact element,
    wherein the contact elements of the contact device are arranged so as to be movable between a contact position and a disconnected position due to movement of the coupling device, and
    wherein when said contact elements are in the contact position, said electrical control unit of micrometering unit is electrically connected to the transmission means of electronic control device and wherein electrical contact electrically connects the micrometering unit to the electronic control device.

2. The pipetting apparatus as claimed in claim 1, wherein a switching device is provided on the micrometering unit or on the holder, said switching device controlling switching between said coupled position and said decoupled position.

3. The pipetting apparatus as claimed in claim 2, wherein the switching device has a movable locking bolt, said locking bolt cooperating with the contact device on the holder.

4. The pipetting apparatus as claimed in claim 1, wherein the coupling device and the counterpart coupling device are movable relative to one another in a joining direction in order to electrically couple the micrometering unit to the pipetting unit.

5. The pipetting apparatus as claimed in claim 1, wherein the micrometering unit has an actuating device for a back and forth movement causing liquid contained in the vessel to be dispensed from the vessel.

6. The pipetting apparatus as claimed in claim 5, comprising a switching device operatively connected to the actuating device of the micrometering unit.

7. The pipetting apparatus as claimed in claim 6, comprising a drive unit for at least one of the switching device and the actuating device, wherein the control unit of the micrometering unit is connected for control purposes to the drive unit.

8. The pipetting apparatus as claimed in claim 7, wherein at least one of the actuating device or the drive unit are controllable by the control unit of the micrometering unit.

9. The pipetting apparatus as claimed in claim 1, wherein the at least one contact element is a spring-mounted contact pin, or inherently resilient contact finger.

10. The pipetting apparatus as claimed in claim 1, wherein the at least one counterpart contact element has a contact face that makes electrical contact with the at least one contact element.

11. The pipetting apparatus as claimed in claim 1, wherein an actuator is provided on the holder or the micrometering unit, said actuator being connected to the control device of the pipetting apparatus for control purposes and to the contact device for drive purposes.

12. The pipetting apparatus as claimed in claim 11, wherein at least one electrical contact element of the contact device is movable away from the counterpart contact device up to a travel limit by the actuator before the micrometering device is coupled to the pipetting unit, and is movable toward the counterpart contact device during or after the coupling of the micrometering unit to the pipetting unit, such that the at least one contact element then comes into engagement with the at least one counterpart contact element so as to make electrical contact.

13. The pipetting apparatus as claimed in claim 1, wherein the micrometering unit coupled to the pipetting unit is movable together with the pipetting unit into spatially different operating positions by means of the positioning device.

* * * * *